United States Patent
Rousseau

(10) Patent No.: US 10,470,760 B2
(45) Date of Patent: Nov. 12, 2019

(54) MODIFIED TISSUE SECUREMENT FIBERS

(75) Inventor: Robert A. Rousseau, Ottsville, PA (US)

(73) Assignee: Ethicon, Inc., Somerville, NJ (US)

( * ) Notice: Subject to any disclaimer, the term of this patent is extended or adjusted under 35 U.S.C. 154(b) by 422 days.

(21) Appl. No.: 13/314,704

(22) Filed: Dec. 8, 2011

(65) Prior Publication Data

US 2013/0150872 A1  Jun. 13, 2013

(51) Int. Cl.
  *A61B 17/06*  (2006.01)
  *A61L 17/04*  (2006.01)
  *A61L 17/12*  (2006.01)

(52) U.S. Cl.
  CPC ........ *A61B 17/06* (2013.01); *A61B 17/06166* (2013.01); *A61L 17/04* (2013.01); *A61L 17/12* (2013.01)

(58) Field of Classification Search
  CPC ..... A61B 17/00; A61B 17/04; A61B 17/0466; A61B 17/06166; A61B 2017/0618; A61B 2017/06185; A61B 2017/06176; A61F 5/56; A61F 5/566; A61F 2/02; A61F 2002/044; A61F 2002/046; A61L 17/00; A61L 17/04; A61L 17/06
  See application file for complete search history.

(56) References Cited

U.S. PATENT DOCUMENTS

| | | |
|---|---|---|
| 2,705,492 A | 4/1955 | Chandler |
| 3,123,077 A | 3/1964 | Alcamo |
| 3,378,010 A | 4/1968 | Codling et al. |
| 4,024,855 A | 5/1977 | Bucalo |
| 4,069,825 A | 1/1978 | Akiyama |
| 4,290,763 A | 9/1981 | Hurst |
| 4,523,584 A | 6/1985 | Lynch |
| 4,557,264 A | 12/1985 | Hinsch |
| 4,839,215 A | 6/1989 | Starling et al. |
| 4,881,939 A | 11/1989 | Newman |
| 4,950,285 A | 8/1990 | Wilk |
| 5,053,047 A | 10/1991 | Yoon |
| 5,067,485 A | 11/1991 | Cowen |
| 5,123,913 A | 6/1992 | Wilk et al. |
| 5,192,271 A | 3/1993 | Kalb et al. |
| 5,192,274 A | 3/1993 | Bierman |
| 5,269,783 A | 12/1993 | Sander |
| 5,284,161 A | 2/1994 | Karell |

(Continued)

FOREIGN PATENT DOCUMENTS

| | | |
|---|---|---|
| CN | 2465680 | 12/2001 |
| CN | 201029957 Y | 3/2008 |

(Continued)

OTHER PUBLICATIONS

MacMillan Dictionary, Fiber , MacMillan Publisher, Limited 2009-2014.*

(Continued)

*Primary Examiner* — Robert A Lynch

(57) ABSTRACT

Tissue securement fibers of reduced cross sectional area and methods of making them are disclosed. The fibers comprising reduced cross sectional areas provide higher degrees of flexibility by providing discrete bending zones most useful in applications when the fiber is bent at an included angle less than 180°, more particularly when the included angle is less than 90°.

15 Claims, 4 Drawing Sheets

(56) References Cited

U.S. PATENT DOCUMENTS

| | | | |
|---|---|---|---|
| 5,311,028 A | 5/1994 | Glavish | |
| 5,393,984 A | 2/1995 | Glavish | |
| 5,483,077 A | 1/1996 | Glavish | |
| 5,484,444 A | 1/1996 | Braunschweiler et al. | |
| 5,609,559 A | 3/1997 | Weitzner | |
| 5,683,417 A | 11/1997 | Cooper | |
| 5,704,895 A | 6/1998 | Scott et al. | |
| 5,792,067 A | 8/1998 | Karell | |
| 5,843,077 A | 12/1998 | Edwards | |
| 5,931,855 A | 8/1999 | Buncke | |
| 6,161,541 A | 12/2000 | Woodson | |
| 6,190,401 B1 | 2/2001 | Green et al. | |
| 6,241,747 B1 | 6/2001 | Ruff | |
| 6,250,307 B1 | 6/2001 | Conrad et al. | |
| 6,348,156 B1 | 2/2002 | Vishnoi et al. | |
| 6,408,851 B1 | 6/2002 | Karell | |
| 6,431,174 B1 | 8/2002 | Knudson et al. | |
| 6,432,437 B1 | 8/2002 | Hubbard | |
| 6,457,472 B1 | 10/2002 | Schwartz et al. | |
| 6,491,714 B1 * | 12/2002 | Bennett | A61F 2/0805 606/232 |
| 6,513,530 B2 | 2/2003 | Knudson et al. | |
| 6,523,542 B2 | 2/2003 | Knudson et al. | |
| 6,578,580 B2 | 6/2003 | Conrad et al. | |
| 6,589,549 B2 | 7/2003 | Shih et al. | |
| 6,599,310 B2 | 7/2003 | Leung et al. | |
| 6,627,600 B2 | 9/2003 | Boutignon | |
| 6,634,362 B2 | 10/2003 | Conrad et al. | |
| 6,638,284 B1 | 10/2003 | Rousseau et al. | |
| 6,716,251 B1 | 4/2004 | Asius et al. | |
| 6,742,524 B2 | 6/2004 | Knudson et al. | |
| 6,755,868 B2 | 6/2004 | Rousseau | |
| 6,800,082 B2 | 10/2004 | Rousseau | |
| 6,899,105 B2 | 5/2005 | Krueger et al. | |
| 6,955,172 B2 | 10/2005 | Nelson et al. | |
| 6,981,944 B2 | 1/2006 | Jamiolkowski et al. | |
| 7,017,582 B2 | 3/2006 | Metzger et al. | |
| 7,056,331 B2 | 6/2006 | Kaplan et al. | |
| 7,135,189 B2 | 11/2006 | Knapp | |
| 7,146,981 B2 | 12/2006 | Knudson et al. | |
| 7,166,570 B2 | 1/2007 | Hunter et al. | |
| 7,213,599 B2 | 5/2007 | Conrad et al. | |
| 7,237,554 B2 | 7/2007 | Conrad et al. | |
| 7,261,702 B1 | 8/2007 | Alexandre et al. | |
| 7,288,075 B2 | 10/2007 | Parihar et al. | |
| 7,297,102 B2 | 11/2007 | Smith et al. | |
| 7,322,993 B2 | 1/2008 | Metzger et al. | |
| 7,337,781 B2 | 3/2008 | Vassallo | |
| 7,360,432 B2 | 4/2008 | Lehtonen | |
| 7,360,542 B2 | 4/2008 | Nelson et al. | |
| 7,367,340 B2 | 5/2008 | Nelson et al. | |
| 7,401,611 B2 | 7/2008 | Conrad et al. | |
| 7,442,389 B2 | 10/2008 | Quelle et al. | |
| 7,601,164 B2 | 10/2009 | Wu | |
| 7,669,603 B2 | 3/2010 | Knudson et al. | |
| 7,806,908 B2 | 10/2010 | Ruff | |
| 7,850,894 B2 | 12/2010 | Lindh, Sr. et al. | |
| 7,857,829 B2 | 12/2010 | Kaplan et al. | |
| 7,888,119 B2 | 2/2011 | Sugaya et al. | |
| 8,142,422 B2 | 3/2012 | Makower et al. | |
| 8,307,831 B2 | 11/2012 | Rousseau | |
| 8,413,661 B2 | 4/2013 | Rousseau et al. | |
| 8,800,567 B2 | 8/2014 | Weadock et al. | |
| 2001/0037133 A1 | 11/2001 | Knudson et al. | |
| 2002/0144685 A1 | 10/2002 | Ivanovich et al. | |
| 2003/0004579 A1 | 1/2003 | Rousseau et al. | |
| 2003/0034312 A1 | 2/2003 | Unger et al. | |
| 2003/0149445 A1 | 8/2003 | Knudson et al. | |
| 2003/0149447 A1 | 8/2003 | Morency et al. | |
| 2003/0149488 A1 | 8/2003 | Metzger et al. | |
| 2003/0176875 A1 | 9/2003 | Anderson et al. | |
| 2004/0020492 A1 | 2/2004 | Dubrul et al. | |
| 2004/0020498 A1 | 2/2004 | Knudson et al. | |
| 2004/0028676 A1 | 2/2004 | Klein et al. | |
| 2004/0044366 A1 | 3/2004 | Bonutti et al. | |
| 2004/0102796 A1 | 5/2004 | Hill et al. | |
| 2004/0153127 A1 | 5/2004 | Gordon et al. | |
| 2004/0139975 A1 | 7/2004 | Nelson et al. | |
| 2004/0144395 A1 | 7/2004 | Evans et al. | |
| 2004/0147811 A1 | 7/2004 | Diederich et al. | |
| 2004/0149290 A1 | 8/2004 | Nelson et al. | |
| 2004/0231678 A1 | 11/2004 | Fierro | |
| 2005/0038472 A1 | 2/2005 | Furst | |
| 2005/0082452 A1 | 4/2005 | Kirby | |
| 2005/0092334 A1 | 5/2005 | Conrad et al. | |
| 2005/0115572 A1 | 6/2005 | Brooks et al. | |
| 2005/0121039 A1 | 6/2005 | Brooks et al. | |
| 2005/0126563 A1 | 6/2005 | van de Burg et al. | |
| 2005/0159637 A9 | 7/2005 | Nelson et al. | |
| 2005/0165352 A1 | 7/2005 | Henry et al. | |
| 2005/0199248 A1 | 9/2005 | Pflueger et al. | |
| 2005/0203576 A1 | 9/2005 | Sulamanidze et al. | |
| 2005/0251255 A1 | 11/2005 | Metzger et al. | |
| 2005/0267321 A1 | 12/2005 | Shadduck | |
| 2005/0267531 A1 | 12/2005 | Ruff et al. | |
| 2005/0267532 A1 | 12/2005 | Wu | |
| 2005/0267571 A1 | 12/2005 | Spence et al. | |
| 2005/0268919 A1 | 12/2005 | Conrad et al. | |
| 2005/0279365 A1 | 12/2005 | Armijo et al. | |
| 2006/0005843 A9 | 1/2006 | Nelson et al. | |
| 2006/0079935 A1 | 4/2006 | Kolster | |
| 2006/0083767 A1 | 4/2006 | Deusch et al. | |
| 2006/0093644 A1 | 5/2006 | Quelle et al. | |
| 2006/0150986 A1 | 7/2006 | Roue et al. | |
| 2006/0185673 A1 | 8/2006 | Critzer et al. | |
| 2006/0206197 A1 | 9/2006 | Morsi | |
| 2006/0207608 A1 | 9/2006 | Hirotsuka et al. | |
| 2006/0207612 A1 | 9/2006 | Jackson et al. | |
| 2006/0228391 A1 | 10/2006 | Seyedin et al. | |
| 2006/0241339 A1 | 10/2006 | Cook et al. | |
| 2006/0266369 A1 | 11/2006 | Atkinson et al. | |
| 2006/0289015 A1 | 12/2006 | Boucher et al. | |
| 2007/0000497 A1 | 1/2007 | Boucher et al. | |
| 2007/0005109 A1 | 1/2007 | Popadiuk et al. | |
| 2007/0005110 A1 | 1/2007 | Collier et al. | |
| 2007/0102004 A1 | 5/2007 | Nelson et al. | |
| 2007/0102010 A1 | 5/2007 | Lemperle et al. | |
| 2007/0110788 A1 | 5/2007 | Hissong et al. | |
| 2007/0119463 A1 | 5/2007 | Nelson et al. | |
| 2007/0123996 A1 | 5/2007 | Sugaya et al. | |
| 2007/0144531 A1 | 6/2007 | Tomas et al. | |
| 2007/0144534 A1 * | 6/2007 | Mery et al. | 128/848 |
| 2007/0144535 A1 | 6/2007 | Hegde et al. | |
| 2007/0144539 A1 | 6/2007 | Dineen et al. | |
| 2007/0186936 A1 | 8/2007 | Nelson et al. | |
| 2007/0190108 A1 | 8/2007 | Datta et al. | |
| 2007/0204866 A1 | 9/2007 | Conrad et al. | |
| 2007/0209665 A1 | 9/2007 | Gillis et al. | |
| 2007/0227545 A1 | 10/2007 | Conrad et al. | |
| 2007/0233276 A1 | 10/2007 | Conrad et al. | |
| 2007/0246052 A1 | 10/2007 | Hegde et al. | |
| 2007/0256693 A1 | 11/2007 | Paraschac et al. | |
| 2007/0257395 A1 * | 11/2007 | Lindh et al. | 264/171.12 |
| 2007/0261701 A1 | 11/2007 | Sanders | |
| 2007/0267027 A1 | 11/2007 | Nelson et al. | |
| 2007/0270631 A1 | 11/2007 | Nelson et al. | |
| 2007/0272257 A1 | 11/2007 | Nelson et al. | |
| 2007/0288057 A1 | 12/2007 | Kuhnel | |
| 2007/0295338 A1 | 12/2007 | Loomas et al. | |
| 2007/0295340 A1 | 12/2007 | Buscemi | |
| 2008/0023012 A1 | 1/2008 | Dineen et al. | |
| 2008/0035158 A1 | 2/2008 | Pflueger et al. | |
| 2008/0035160 A1 | 2/2008 | Woodson et al. | |
| 2008/0053461 A1 | 3/2008 | Dineen et al. | |
| 2008/0066764 A1 | 3/2008 | Paraschac et al. | |
| 2008/0066765 A1 | 3/2008 | Paraschac et al. | |
| 2008/0066766 A1 | 3/2008 | Paraschac et al. | |
| 2008/0066767 A1 | 3/2008 | Paraschac et al. | |
| 2008/0066769 A1 | 3/2008 | Dineen et al. | |
| 2008/0078411 A1 | 4/2008 | Buscemi et al. | |
| 2008/0146868 A1 | 6/2008 | Robert et al. | |
| 2008/0167614 A1 | 7/2008 | Tolkowsky et al. | |
| 2008/0199824 A1 | 8/2008 | Hargadon | |
| 2008/0208265 A1 | 8/2008 | Frazier et al. | |

(56) References Cited

U.S. PATENT DOCUMENTS

| | | |
|---|---|---|
| 2008/0221684 A1 | 9/2008 | Nelson et al. |
| 2008/0312688 A1 | 12/2008 | Nawrocki et al. |
| 2009/0025734 A1 | 1/2009 | Doelling et al. |
| 2009/0078411 A1 | 3/2009 | Kenison et al. |
| 2009/0165803 A1 | 7/2009 | Bhat et al. |
| 2010/0023055 A1* | 1/2010 | Rousseau ............ 606/228 |
| 2010/0024830 A1 | 2/2010 | Rousseau et al. |
| 2010/0030011 A1 | 2/2010 | Weadock et al. |
| 2010/0037901 A1 | 2/2010 | Rousseau et al. |
| 2010/0049227 A1 | 2/2010 | Hedge et al. |
| 2010/0080791 A1 | 4/2010 | Rousseau et al. |
| 2010/0106246 A1 | 4/2010 | Rousseau et al. |
| 2010/0108077 A1 | 5/2010 | Lindh et al. |
| 2010/0132719 A1 | 6/2010 | Jacobs et al. |
| 2010/0137794 A1 | 6/2010 | Knudson et al. |
| 2010/0137905 A1 | 6/2010 | Weadock et al. |
| 2010/0158854 A1 | 6/2010 | Puisais |
| 2010/0163056 A1* | 7/2010 | Tschopp et al. ............ 128/848 |
| 2010/0211184 A1 | 8/2010 | Rousseau et al. |
| 2010/0234794 A1 | 9/2010 | Weadock et al. |
| 2010/0234946 A1 | 9/2010 | Rousseau |
| 2010/0256443 A1 | 10/2010 | Griguol |
| 2010/0294284 A1 | 11/2010 | Hohenhorst et al. |
| 2010/0319710 A1 | 12/2010 | Sharkawy et al. |
| 2011/0054522 A1 | 3/2011 | Lindh et al. |
| 2011/0100376 A1 | 5/2011 | Rousseau |
| 2011/0100377 A1 | 5/2011 | Weadock et al. |
| 2011/0100378 A1 | 5/2011 | Rousseau |
| 2011/0144558 A1 | 6/2011 | Rousseau |
| 2011/0174315 A1 | 7/2011 | Zhang et al. |
| 2011/0178439 A1 | 7/2011 | Irwin et al. |
| 2011/0238111 A1 | 9/2011 | Frank |
| 2011/0245850 A1 | 10/2011 | Cheng et al. |
| 2011/0282386 A1 | 11/2011 | Friedrich |
| 2011/0288583 A1* | 11/2011 | Goraltchouk .... A61B 17/06166 606/228 |
| 2012/0123449 A1 | 5/2012 | Schaller et al. |
| 2012/0160249 A1 | 6/2012 | Garrett |
| 2012/0245629 A1 | 9/2012 | Gross et al. |
| 2013/0074849 A1 | 3/2013 | Rousseau et al. |
| 2013/0098371 A1 | 4/2013 | Rousseau et al. |
| 2013/0103078 A1 | 4/2013 | Crovella et al. |
| 2013/0118505 A1 | 5/2013 | Rousseau et al. |
| 2013/0133669 A1 | 5/2013 | Rousseau |
| 2013/0150872 A1 | 6/2013 | Rousseau |
| 2013/0174857 A1 | 7/2013 | Rousseau et al. |
| 2013/0186412 A1 | 7/2013 | Weadock et al. |
| 2013/0319427 A1 | 12/2013 | Sung et al. |

FOREIGN PATENT DOCUMENTS

| | | |
|---|---|---|
| CN | 102198010 A | 9/2011 |
| CN | 102271624 A | 12/2011 |
| DE | 10245076 A1 | 4/2004 |
| EP | 2145587 A2 * | 1/2010 |
| EP | 2386252 A1 | 11/2011 |
| EP | 2517633 A1 | 10/2012 |
| FR | 2651113 A1 | 3/1991 |
| JP | 7-500386 | 1/1995 |
| JP | 11-514266 | 12/1999 |
| JP | 2001-145646 | 5/2001 |
| JP | 2002-506376 | 2/2002 |
| JP | 2003265621 | 9/2003 |
| JP | 2005-518899 | 6/2005 |
| JP | 2005-529643 | 10/2005 |
| JP | 2006-507038 | 3/2006 |
| JP | 2006-508708 | 3/2006 |
| JP | 2006-517115 | 7/2006 |
| JP | 38-28508 | 10/2006 |
| JP | 2007-512090 | 5/2007 |
| JP | 2007-313337 | 12/2007 |
| JP | 2008-526286 | 7/2008 |
| JP | 2008-529608 | 8/2008 |
| JP | 2009-006090 A | 1/2009 |
| JP | 2010-017560 | 1/2010 |
| JP | 44-14959 | 2/2010 |
| JP | 2011-502549 | 1/2011 |
| JP | 2011-530385 | 12/2011 |
| JP | 2012-507356 | 3/2012 |
| RU | 2005447 C1 | 1/1994 |
| RU | 2202313 C2 | 4/2003 |
| SU | 927236 B | 5/1982 |
| SU | 1697792 A1 | 12/1991 |
| WO | WO 1997/13465 | 4/1997 |
| WO | WO 1999/000058 A1 | 1/1999 |
| WO | WO 2000/066050 | 11/2000 |
| WO | WO 2001/021107 A1 | 3/2001 |
| WO | WO 2003/075792 | 9/2003 |
| WO | WO 2003/096928 A1 | 11/2003 |
| WO | WO 2004/016196 A2 | 2/2004 |
| WO | WO 2004/016196 A3 | 2/2004 |
| WO | WO 2004/021869 A2 | 3/2004 |
| WO | WO 2004/021870 A2 | 3/2004 |
| WO | WO 2004/021870 A3 | 3/2004 |
| WO | WO 2004/060311 A2 | 7/2004 |
| WO | WO 2004/060311 A3 | 7/2004 |
| WO | WO 2004/084709 A2 | 10/2004 |
| WO | WO 2004/084709 A3 | 10/2004 |
| WO | WO 2004/103196 | 12/2004 |
| WO | WO 2005/046554 A2 | 5/2005 |
| WO | WO 2005/046554 A3 | 5/2005 |
| WO | WO 2005/051292 A2 | 6/2005 |
| WO | WO 2005/082452 A1 | 9/2005 |
| WO | WO 2005/122954 A1 | 12/2005 |
| WO | WO 2006/012188 A1 | 2/2006 |
| WO | WO 2004/020492 | 4/2006 |
| WO | WO 2006/072571 A1 | 7/2006 |
| WO | WO 2006/108145 A1 | 10/2006 |
| WO | WO 2007/056583 A1 | 5/2007 |
| WO | WO 2007/075394 A2 | 7/2007 |
| WO | WO 2007/075394 A3 | 7/2007 |
| WO | WO 2007/132449 A2 | 11/2007 |
| WO | WO 2007/132449 A3 | 11/2007 |
| WO | WO 2007/134005 A1 | 11/2007 |
| WO | WO 2007/146338 A2 | 12/2007 |
| WO | WO 2007/149469 A2 | 12/2007 |
| WO | WO 2007/149469 A3 | 12/2007 |
| WO | WO 2008/042058 | 4/2008 |
| WO | WO 2008/063218 | 5/2008 |
| WO | WO 2008/118913 A2 | 10/2008 |
| WO | WO 2009/023256 A2 | 10/2008 |
| WO | WO 2009/036094 A2 | 2/2009 |
| WO | WO 2010/065341 A2 | 3/2009 |
| WO | WO 2010/065341 A3 | 3/2009 |
| WO | WO 2010/019376 A2 | 2/2010 |
| WO | WO 2010/035303 A1 | 4/2010 |
| WO | WO 2010/051195 | 5/2010 |
| WO | WO 2011058340 A1 * | 5/2011 ........... A61F 2/0045 |
| WO | WO 2012/004758 | 1/2012 |
| WO | WO 2012/041205 A1 | 4/2012 |
| WO | WO 2012/064902 A2 | 5/2012 |
| WO | WO 2012/170468 | 12/2012 |

OTHER PUBLICATIONS

Cole et al., "Snoring: A Review and a Reassessment", J. of Otolaryngology, vol. 24, No. 5 pp. 303-306 (1995).

Harries et al., "The Surgical treatment of snoring", J. of Laryngology and Otology, vol. 110, Issue 12 pp. 1105-1106 (1996).

Huang et al., "Biomechanics of snoring", Endeavour, vol. 19(3): pp. 96-100 (1995).

Pang, Kenny et al., "Tongue Suspension Suture in Obstructive Sleep Apnea", Operative Techniques in Otolaryngology, vol. 17, No. 4, pp. 252-256 (2006).

Repose Genioglossus Advancement, Influent Medical, www.influent.com, 1 page (2008).

Schleef et al., "Cytokine Activation of Vascular Endothelium, Effects on Tissue-Type 1 Plasminogen Activator Inhibitor" The J. of Biological Chem., vol. 263, No. 12, pp. 5797-5803 (1988).

Schwab et al., "Upper airway and soft tissue changes induced by CPAP in normal subject", Am. J. Respit. Crit. Care Med., vol. 154, No. 4 pp. 1106-1116 (1996).

(56) References Cited

OTHER PUBLICATIONS

Schwartz et al., "Effects of electrical stimulation to the soft palate on snoring and obstructive sleep apnea", J. Prosthetic Dentistry, vol. 76 pp. 273-281 (1996).
Shamsuzzaman et al., "Obstructive Sleep Apnea; Implications for Cardiac and Vascular Disease", JAMA vol. 290, No. 14 pp. 1906-1914 (2003).
Teles et al., "Use of Palatal Lift Prosthesis on Patient Submitted to Maxillectomy: A Case Report", Applied Cancer Res. vol. 25(3), pp. 151-154 (2005).
The Advance System, Aspire Medical, Inc. www.aspiremedical.com, 3 pp (2008).
The Pillar Procedure, Restore Medical, Inc. www.restoremedical.com, 2 pp (2008).
Vicente et al., "Tongue-Base Suspension in Conjunction with Uvulopapatopharyngoplasty for Treatment of Severe Obstructive Sleep Apnea: Long-term Follow-Up Results", The Laryngoscope, vol. 116 pp. 1223-1227 (2006).
Wassmuth et al., "Cautery-assisted palatal stiffening operation for the treatment of obstructive sleep apnea syndrome", Otolaryngology—Head and Neck Surgery, vol. 123, pp. 55-60 (2000).
Wiltfang et al., "First results on daytime submandibular electrostimulation of suprahyoidal muscles to prevent night-time hypopharyngeal collapse in obstructive sleep apnea syndrome", Intl J. of Oral & Maxillofacial Surgery vol. 28 pp. 21-25 (1999).
Database WPI Week 198312, Thomson Scientific, London, GB; AN 1983-D9513K XP002693421, -& SU 927 236 A1 (Petrozazodsk Univ) May 15, 1982 (May 15, 1982) abstract (see figures 7 & 8).
Friedman et al., "A System and Method for Inserting a Medical Device for Treatment of Sleep Apnea via the Nasal Passage, and Device Therefor", Dec. 29, 2008, U.S. Appl. No. 61/203,758, p. 8 & p. 6/8.
Medtronic AIRvance System for Obstructive Sleep Apnea. http://www.medtronic.com/for-healthcare-professionals/products-therapies/ear-nose-throat/sleep-disordered-breathing-products/airvance-system-for-obstructive-sleep-apnea/index.htm.
U.S. Appl. No. 13/784,077, filed Mar. 4, 2013 published 2013/0174857.
U.S. Appl. No. 12/578,271, filed Oct. 13, 2009 published 2010/0137905.
U.S. Appl. No. 13/790,509, filed Mar. 8, 2013 published 2013/0186412.
U.S. Appl. No. 13/735,766, filed Jan. 7, 2013 published 2013/0118505.
U.S. Appl. No. 12/404,377, filed Mar. 16, 2009 published 2010/0234946; issued U.S. Pat. No. 8,307,831.
U.S. Appl. No. 12/608,057, filed Oct. 29, 2009 published 2011/0100376.
U.S. Appl. No. 12/638,492, filed Dec. 15, 2009 published 2011/0144558.
U.S. Appl. No. 12/609,424, filed Oct. 30, 2009 published 2011/0100378.
U.S. Appl. No. 12/608,168, filed Oct. 29, 2009 published 2011/0100377.
U.S. Appl. No. 13/307,482, filed Nov. 30, 2011 *published as US 2013/0133669.
U.S. Appl. No. 13/486,293, filed Jun. 1, 2012* published as US 2013/0319427.
International Search Report re: PCT/US2012/0565677 dated Nov. 27, 2012.
International Search Report dated Apr. 9, 2013 for International Patent Application No. PCT/US2012/061569.
International Search Report dated Apr. 2, 2013 for International Patent Application No. PCT/US2012/067708.
International Search Report dated Oct. 2, 2013 re: PCT/US2013/043238.
International Search Report dated May 24, 2013 for International Patent Application No. PCT/US2012/066011.
Written Opinion dated Nov. 27, 2012 for International Patent Application No. PCT/US2012/056577.

U.S. Appl. No. 12/182,402, filed Jul. 30, 2008.
U.S. Appl. No. 12/183,955, filed Jul. 31, 2008.
U.S. Appl. No. 12/228,681, filed Aug. 14, 2008.
U.S. Appl. No. 12/238,991, filed Sep. 26, 2008.
U.S. Appl. No. 12/257,563, filed Oct. 24, 2008.
U.S. Appl. No. 12/261,102, filed Oct. 30, 2008.
U.S. Appl. No. 12/325,350, filed Dec. 1, 2008.
U.S. Appl. No. 12/378,573, filed Feb. 17, 2009.
U.S. Appl. No. 12/402,631, filed Mar. 12, 2009.
U.S. Appl. No. 13/247,713, filed Sep. 28, 2011.
U.S. Appl. No. 13/279,384, filed Oct. 24, 2011.
U.S. Appl. No. 13/314,704, filed Dec. 8, 2011.
Notification of Transmittal of the International Search Report and the Written Opinion of the International Search Authority or the Declaration dated Feb. 3, 2010; PCT/US2009/051921; International Filing Date: Jul. 28, 2009.
Notification of Transmittal of the International Search Report and the Written Opinion of the International Search Authority or the Declaration dated May 25, 2010; PCT/US2010/023152; International Filing Date: Apr. 2, 2010.
International Search Report dated Nov. 4, 2009 for International Patent Application No. PCT/US2009/052126.
International Search Report dated Dec. 21, 2009 for International Patent Application No. PCT/US2009/057661.
International Search Report dated Dec. 22, 2009 for International Patent Application No. PCT/US2009/061223.
International Search Report dated Dec. 29, 2009 for International Patent Application No. PCT/US2009/061455.
International Search Report dated Jan. 21, 2010 for International Patent Application No. PCT/US2009/052110.
International Search Report dated Apr. 29, 2010 for International Patent Application No. PCT/US2009/065293.
International Search Report dated May 25, 2010 for International Patent Application No. PCT/US2010/023152.
International Search Report dated May 25, 2010 for International Patent Application No. PCT/US2010/025778.
International Search Report dated Jan. 14, 2011 for International Patent Application No. PCT/US2010/052628.
International Search Report dated Jan. 20, 2011 for International Patent Application No. PCT/US2010/052644.
International Search Report dated Jan. 24, 2011 for International Patent Application No. PCT/US2010/052649.
International Search Report dated Feb. 28, 2011 for International Patent Application No. PCT/US2010/059673.
Nordgard, S. et al 'One-year results: palatal implants for the treatment of obstructive sleep apnea' Otolaryngology Head Neck Surg. May 2007; 136(5): 818-22.
International Preliminary Report on Patentability dated Feb. 1, 2011 for International Patent Application No. PCT/US2009/052110.
International Preliminary Report on Patentability dated Feb. 1, 2011 for International Patent Application No. PCT/US2009/052126.
International Preliminary Report on Patentability dated Feb. 15, 2011 for International Patent Application No. PCT/US2009/051921.
International Preliminary Report on Patentability dated Apr. 26, 2011 for International Patent Application No. PCT/US2009/061223.
International Preliminary Report on Patentability dated May 3, 2011 for International Patent Application No. PCT/US2009/061455.
International Preliminary Report on Patentability dated Jun. 7, 2011 for International Patent Application No. PCT/US2009/065293.
International Preliminary Report on Patentability dated Aug. 23, 2011 for International Patent Application No. PCT/US2010/023152.
International Preliminary Report on Patentability dated Sep. 20, 2011 for International Patent Application No. PCT/US2010/025778.
International Preliminary Report on Patentability dated May 1, 2012 for International Patent Application No. PCT/US2010/052628.
International Preliminary Report on Patentability dated May 1, 2012 for International Patent Application No. PCT/US2010/052644.
International Preliminary Report on Patentability dated May 1, 2012 for International Patent Application No. PCT/US2010/052649.
International Preliminary Report on Patentability dated Jun. 19, 2012 for International Patent Application No. PCT/US2010/059673.

(56) References Cited

OTHER PUBLICATIONS

International Preliminary Report on Patentability dated Apr. 1, 2014 for International Patent Application No. PCT/US2012/056577.
International Preliminary Report on Patentability dated Apr. 29, 2014 for International Patent Application No. PCT/US2012/061569.
International Preliminary Report on Patentability dated Jun. 3, 2014 for International Patent Application No. PCT/US2012/066011.
International Preliminary Report on Patentability dated Jun. 10, 2014 for International Patent Application No. PCT/US2012/067708.
International Preliminary Report on Patentability dated Dec. 2, 2014 for International Patent Application No. PCT/US2013/043238.
International Search Report dated Mar. 2, 2010 for International Patent Application No. PCT/US2009/051921.

* cited by examiner

MODIFIED TISSUE SECUREMENT FIBERS

BACKGROUND OF THE INVENTION

1. Field of the Invention

This invention generally relates to systems to secure tissue, more particularly to tissue securement fibers comprising section(s) of reduced cross sectional area (compared to the cross sectional area of the rest of the fiber) useful in applications wherein the path of the securement fiber is bent at included angles less than 180°, more particularly when the included angle is less than 90°.

2. Related Art

Obstructive sleep apnea (OSA) is caused by a blockage of the airway, which usually occurs when the soft tissue in the throat collapses and closes during sleep. According to the National Institutes of Health, OSA affects more than twelve million Americans. During each apnea event, the brain briefly arouses the sufferer in order to initiate the resumption of breathing. This type of sleep, however, is extremely fragmented and of poor quality. When left untreated, OSA may result in high blood pressure, cardiovascular disease, weight gain, impotency, headaches, memory problems, job impairment, and motor vehicle crashes. Despite the seriousness of OSA, a general lack of awareness among the public and healthcare professionals results in the vast majority of OSA sufferers remaining undiagnosed and untreated.

One non-surgical method available to treat OSA, commonly referred to as continuous positive airway pressure (CPAP), delivers air into a patient's airway through a specially designed nasal mask or pillow. The flow of air creates positive pressure when the patient inhales to keep the airway open. CPAP is considered by many to be an effective non-surgical treatment for the alleviation of snoring and obstructive sleep apnea, however, patients complain about discomfort caused by the mask and hoses, including bloating, nasal drying, and dry eyes. As a result, patient compliance for CPAP is only about 40%.

Surgical treatments have also been used to treat OSA. One such treatment is referred to as uvulopalatopharyngoplasty, which involves removing about 2 cm of the trailing edge of the soft palate to reduce the soft palate's ability to flutter between the tongue and the pharyngeal wall. Another procedure uses a surgical laser to create scar tissue on the surface of the soft palate, which reduces the flexibility of the soft palate for reducing snoring and/or closing of the air passage. Yet another procedure, commonly referred to as cautery-assisted palatal stiffening operation (CAPSO), is an office-based procedure performed under local anesthesia whereby a midline strip of soft palate mucosa is removed, and the wound is allowed to heal whereupon the flaccid palate is stiffened.

Surgical procedures such as those mentioned above continue to have challenges. More specifically, the area of tissue that is surgically treated (i.e., removal of palatal tissue or scarring of palatal tissue) is often larger than is necessary to treat the patient's condition. In addition, the above-mentioned surgical procedures are often painful with extended, uncomfortable healing periods. For example, scar tissue on the soft palate may be a cause of continuing irritation to the patient. Furthermore, the above procedures are not reversible in the event of adverse side effects.

Another implant system, sold under the trademark REPOSE™ by InfluENT of Concord, N.H., uses a titanium screw that is inserted into the posterior aspect of the mandible at the floor of the mouth. The screw acts as an anchor. A loop of suture is passed through the tongue base and attached to the mandibular bone screw. The REPOSE™ procedure achieves a suspension or hammock of the tongue base making it less likely for the base of the tongue to prolapse into the patient's airway during sleep. Due to the high activity of the tongue during wakefulness, however, the suture component of this device may act as a cutting element within the tongue, causing device trans-location and ultimately a loss of efficacy of the procedure thereby requiring subsequent removal.

An additional tongue suspension device developed by ASPIRE Medical is named the ADVANCE System. It is similar to the REPOSE suture suspension system for the tongue base in that it utilizes a bone screw in the mandible as an anchor, but has the advantage of being adjustable. The device further utilizes a flexible shape memory soft tissue anchor within the tongue that is shaped similar to a grappling hook, to engage the tissue within the tongue base. The soft tissue anchor is placed through a small incision in the submental region of the patient's head and the suture is attached to a spool-like component attached to the mandible. Two to four weeks after healing, a small incision is made under the chin and a screw is turned to tighten the suture, thus pulling the base of the tongue forward. While the device provides a simplified installation technique from within the sterile space, the anchors may suffer from device fracture and failure due to loading within the tongue musculature.

A further system is disclosed in US 2008/0208265, Frazier, et al., entitled "System and Method for Percutaneous Palate Remodeling". This publication discloses a looped tether element with one or more regions of an expanded diameter to reduce the risk of cutting through the tongue. This region is created to provide a flexible implant with a fixed expanded region, a balloon region or an in-situ expanding region. This method provides a large bearing surface on limited regions of the fiber. Additionally, this method requires a supplemental element to create the expanded region on the fiber. It is anticipated that this type of device will also be difficult to extract from tongue tissues after healing has occurred since the portion buried on the tongue base is larger in cross section than the tracks remaining from the trailing ends of the looped tether.

In spite of the above advances in tongue suspension devices, there remains a need for tongue suspension systems, devices and other tissue suspension devices that provide a high degree of flexibility. Such new systems, devices and methods for treating OSA through minimally invasive approaches will improve long term results with improved patient compliance and minimized patient discomfort.

SUMMARY OF THE INVENTION

The present invention generally relates to tissue securement fibers comprising:

at least one section having a first cross sectional area;

at least one section having a second cross sectional area; and wherein the second cross sectional area is less than the first cross sectional area and the at least one section having the second cross sectional area is intermediate to the at least one section having the first cross sectional area.

In other embodiments the fibers comprise biocompatible materials that can be bioabsorbable, non-bioabsorbable or combinations thereof.

In further embodiments the second cross sectional area comprises an arc, crease, or indentation to facilitate bending of the fiber.

The devices and methods of this invention provide securement fibers having discrete locations of reduced cross sectional area and provide at least the following advantages: (i) reduction of the volume of fiber at critical bend locations; (ii) minimization of tendency for "tissue propping" at puncture sites (i.e., tendency of tissue puncture sites to remain in an expanded or open condition due to volume of fiber present at fiber bend site); and (iii) provision of a natural hinge point to reduce necessary bend radius and reduce volume of fiber at the bend point.

DETAILED DESCRIPTION OF PREFERRED EMBODIMENTS OF THE INVENTION

This invention is directed to tissue securement fibers having section(s) of reduced cross sectional area, particularly fibers useful as tongue suspension fibers for the treatment of OSA and other procedures involving the suspension of tissue in a living being. Generally, the features disclosed herein describe treatment of fibers that are manufactured with a cross-sectional area that is modified through secondary processing to provide discreet bending zones which provide implants of improved local conformability to the desired fiber path or tissue tract. Thus the fibers may be described as monolithic, in the sense they are of unitary construction without the various sections being joined together.

Figure 1:
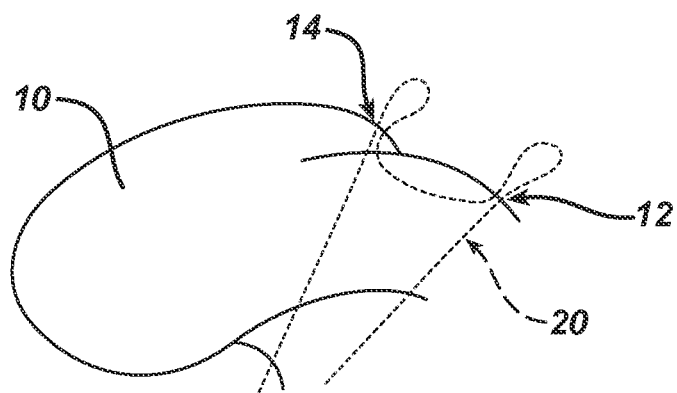
FIG. 1 depicts one potential pathway of a tissue securement fiber for the purpose of securing a tongue.
Figure 2:
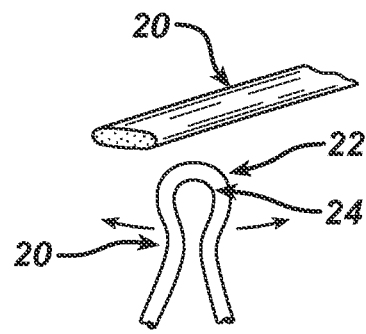
FIG. 2 depicts a typical securement fiber in both unbent and bent configurations.
Figure 3:
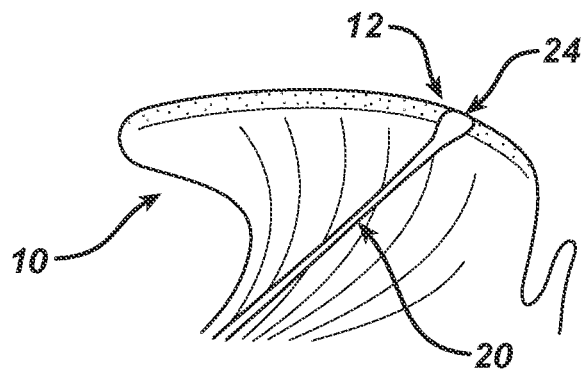
FIG. 3 shows an unmodified tissue securement fiber propping through a tissue puncture site on a tongue.

FIGS. 1-3 depict various aspects of tissue securement methods and devices that result when using securement fibers of unmodified cross sectional area.

Referring to FIG. 1, a securement fiber pathway is illustrated for potential securement of a tongue 10. As can be seen, the dotted pathway for securement fiber 20 through tongue 10 is fairly circuitous. In particular, points 12 and 14 depict tissue puncture points where the securement fiber exits and reenters tongue 10. Since each leg of the fiber is installed within the tissue tract through the exit and re-entry of a discrete puncture site, extremely sharp bends are formed in the securement fiber. Additionally, the relatively small included bend angle of the securement fiber at these points, as shown in FIG. 2, results in a large volume of fiber 22 occurring at the bend at point 24 of fiber 20. The folding of the securement fiber creates a high stress condition in the folded securement fiber which results in an opening or expansion force exerted by the fiber on the local tissue. The expansion force of the securement fiber is depicted by the arrows on either side of fiber 20 in FIG. 2.

FIG. 3 depicts a cross-sectional view of tongue 10 with an unmodified tissue securement fiber 20 propping through tissue puncture site 12 due to the bending of fiber 20 at bend 24 as described in the discussion of FIG. 2.

The following sections describe how the tissue securement fiber's cross sectional area may be reduced for biocompatible materials that can be bioabsorbable, non-bioabsorbable or combinations thereof.

As used herein, the reduction of the securement fiber's cross sectional area may be reported as a reduced cross sectional area or may be referenced to as a reduction of diameter or equivalent diameter of the fiber. For example, for fibers of circular or substantially circular diameter, a reduction in the cross sectional diameter $D_2$ will be equal to the square root of the ratio of reduced cross sectional area ($A_2$) to the original cross sectional area ($A_1$) multiplied by the fiber's original diameter ($D_1$) as derived below:

$$A_1 = \Pi/4 \cdot D_1^2$$

$$A_2 = \Pi/4 \cdot D_2^2$$

$$D_2^2 = A_2/A_1 \cdot D_1^2$$

$$D_2 = D_1 \cdot (A_2/A_1)^{1/2}$$

For elliptical cross sections (for the premise that fiber will be bent across the minor diameter of the ellipse) the reduced minor diameter of $D_{2minor}$ will be equal to the ratio of reduced cross sectional area ($A_2$) to the original cross sectional area ($A_1$) multiplied by the fiber's original minor diameter ($D_{1minor}$) and further multiplied by the ratio of fiber's original major diameter ($D_{1major}$) to the fiber's reduced major diameter ($D_{2major}$) as derived below:

$$A_1 = \Pi \cdot D_{1minor}/2 \cdot D_{1major}/2$$

$$A_2 = \Pi \cdot D_{2minor}/2 \cdot D_{2major}/2$$

$$D_{2minor} = A_2/A_1 \cdot D_{1minor} \cdot D_{1major}/D_{2major}$$

For other cross sectional geometries such as squares, rectangles, stars, other polygonal shapes and for irregular cross sections (for which an equivalent cross sectional diameter may be determined by methods known to those of skill in the art), determination of reduced diameters may be determined by following the methodology as provided above for the circular and elliptical cross sectional areas calculations.

A. Securement Fibers of Reduced Diameters Through Drawing of Fiber

The method for reducing fiber diameter by drawing the fibers utilizes fibers that are produced with substantially uniform large cross sectional areas such as full round or other non-round cross-sectional geometries such as elliptical or rectangular, for example. The fibers may be produced as standard solid form extrusions from a variety of polymeric materials. Suitable non-absorbable materials for use in the present invention include, but are not limited to, polyamides (e.g., polyhexamethylene adipamide (nylon 66), polyhexamethylene sebacamide (nylon 610), polycapramide (nylon 6), polydodecanamide (nylon 12) and polyhexamethylene isophthalamide (nylon 61) copolymers and blends thereof), polyesters (e.g., polyethylene terephthalate, polybutyl terephthalate, copolymers and blends thereof), fluoropolymers (e.g., polytetrafluoroethylene and polyvinylidene fluoride) Poly (hexafluoropropylene-VDF), polyaryletherketones, polyolefins (e.g., polypropylene including isotactic and syndiotactic polypropylene and blends thereof, as well as, blends composed predominately of isotactic or syndiotactic polypropylene blended with heterotactic polypropylene and/or polyethylene (such as is described in U.S. Pat. No. 4,557,264 issued Dec. 10, 1985, assigned to Ethicon, Inc., hereby incorporated by reference in its entirety)) and combinations thereof.

Additionally, bioabsorbable materials may be used to provide temporary suspension fibers. Bioabsorbable fibers are useful such as in the case of trauma, or radical surgical interventions that may cause swelling of the tongue and associated tissues, or in other locations such as urethra suspension, to provide temporary support until edema/swelling has been reduced. Suitable bioabsorbable materials for use as securement fibers include, but are not limited to, aliphatic polyesters which include but are not limited to homopolymers and copolymers of lactide (which includes lactic acid, d-,l- and meso lactide), glycolide (including glycolic acid), ε-caprolactone, p-dioxanone (1,4-dioxan-2-one), trimethylene carbonate (1,3-dioxan-2-one), alkyl derivatives of trimethylene carbonate, δ-valerolactone, β-butyrolactone, γ-butyrolactone, ε-decalactone, hydroxybutyrate, hydroxyvalerate, 1,4-dioxepan-2-one (including its dimer 1,5,8,12-tetraoxacyclotetradecane-7,14-dione), 1,5-dioxepan-2-one, 6,6-dimethyl-1,4-dioxan-2-one and polymer blends thereof.

Combinations of absorbable and non-absorbable materials may also be utilized to produce fibers with tailored properties and configurations. One such configuration contemplated is one which provides fibers with absorbable coverings obtained through processing such as by coating and/or co-extrusion.

Of the foregoing materials, the preferred fiber materials include polyesters (e.g. polyethylene terephthalate, polybutyl terephthalate, copolymers and blends thereof), fluoropolymers (e.g. polytetrafluoroethylene and polyvinylidene fluoride) Poly (hexafluoropropylene-VDF), polyaryletherketones, polyolefins (e.g. polypropylene including isotactic and syndiotactic polypropylene. The most preferred materials are poly (hexafluoropropylene-VDF) and polypropylene.

The conversion of the raw pelletized thermo-plastic polymers into a final fibrous form typically involves thermal melting and extrusion of the raw polymer through an extrusion die to form a particular cross sectional geometry such as square, rectangular, circular, elliptical, star or other polygonal shapes. As the material exits the face of the extrusion die, the polymer enters a quench tank to provide cooling and solidification of the extruded fiber. The fiber is then passed sequentially over a series of heated godets typically rotating with advancing rates of rotation and operating at temperatures above the glass transition temperature of the material and less than the melting temperature of the polymer being processed, for instance in the case of polypropylene, the preferred working temperatures are from 130° C. to 165° C. The differential speeds of rotation, combined with the thermal energy provide for a stretching, or drawing, of the extruded fiber. The fiber may then be subsequently relaxed by passage through a heated chamber and passage over a final godet that is rotating at a speed less than the preceding godet in the system. This stretching of the fiber imparts increasing orientation of the molecular structure of the fiber, increasing the yield strength and rigidity or modulus of elasticity E of the fiber. As the orientation of the fiber is increased, the elongation of the fiber at high stress is also reduced. The relaxation step of the fiber is performed to slightly reduce the orientation of the polymer chains to provide improved flexibility and elongation of the fiber.

The stretching or drawing of the fiber is typically stated as the draw ratio of the fiber which is typically calculated from the linear increase in length of the fiber due to the various speeds of the godets and is stated as a factor of the total elongation vs. the initial length of the undrawn fiber. For example, a polymer is subjected to extrusion and the fiber is passed over three godets A, B and C rotating at progressively increasing speeds $V_A$, $V_B$ and $V_C$ respectively and a fourth godet, D, rotating at a slightly lower speed $V_D$ than the third godet in the system. The draw ratio would be calculated as:

$$\text{Draw Ratio} = (V_A/V_A) * (V_C/V_B) * (V_D/V_C) \text{ or } (V_D/V_A)$$

Alternatively, the use of the distance traveled instead of differential velocity of the godets may also be utilized. In this case, the velocity based equation is converted to the linear distance though the application of the time element. The distance traveled is equal to the velocity of the specific godet multiplied by the time, T that the process has run. Since the time element is fixed for all of the godets in the system, the draw ratio may be expressed more simply as the length of fiber at the completion of drawing ($L_4$) divided by the length of fiber at the initiation to the drawing process ($L_1$).

For example, if godet one is operating at 3 feet per second, and godet four is operating at a speed of 9 feet per second, the resultant draw ratio is equal to (9/3) or 3/1 expressed as 3:1.

An alternative method of assessing the draw ratio would be based upon the ratio of the orifice diameter, for a round fiber, of the extrusion die vs. the final diameter of the final fiber and is defined as the draw down ratio. In this instance the volume of the fiber must remain constant and, for a round fiber, the draw down ratio can be calculated directly from the draw ratio by applying the volume VO equations where:

$$VO_1 = VO_2$$

$$pD_1^2 * L_1/4 = pD_4^2 * L_4/4$$

$$D_1^2 * L_1 = D_4^2 * L_4$$

$$L_1/L_4 = D_4^2/D_1^2$$

Therefore, to calculate the final diameter fiber the die face orifice diameter, coupled with the draw ratio are applied. For example, in the previous example, if the die face diameter is 0.065", and the draw ratio is 3:1 and these factors are applied, the final diameter of the fiber is calculated as:

$$1/3 = D_4^2/(0.065)^2$$

$$(1/3) * (0.065)^2 D_4^2$$

$$0.037" = D_4$$

When materials are extruded to a particular size and shape, the fiber may be produced with a low or minimal draw ratio, approaching a ratio of 1, to provide fibers with greater elongation, reduced notch sensitivity and reduced stiffness when compared to fibers of the same diameter with greater draw ratio's.

Figure 4A:
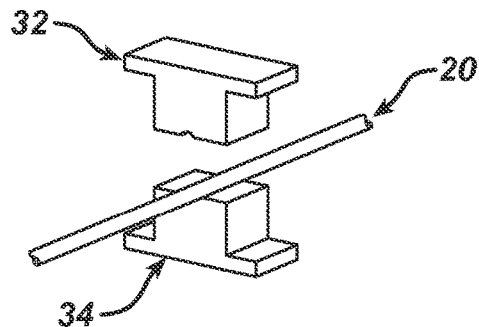
FIGS. 4*a*-4*d* depict one method of reducing the cross sectional area of a tissue securement fiber as well as a tissue securement fiber of reduced cross sectional area.
Figure 4B:
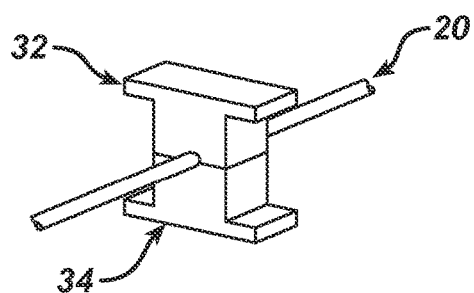
Figure 4C:
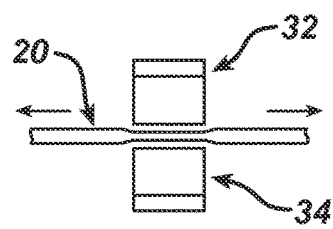
Figure 4D:
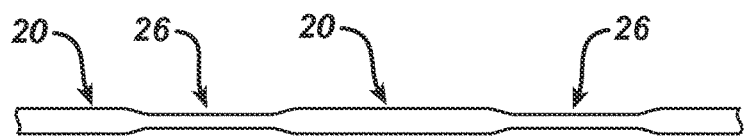

The method of localized fiber diameter reduction by drawing the fiber comprises subjecting a portion of the fiber to localized heating at a particular location and then applying tension to the section of fiber extending from the locally heated section of fiber. Referring to FIG. 4a, heated or energized dies 32 and 34 dies are provided and come into contact with each other and with fiber 20 as seen in FIG. 4b. Once the local regions of fiber 20 have been sufficiently heated, tension is applied to the free ends of the fiber 20 and fiber 20 is drawn to reduce the diameter of the fiber in discrete heated locations as in shown in FIG. 4c. The resulting fiber 20 is shown in FIG. 4d with the distinct sections 26 of reduced diameter.

Figure 6:
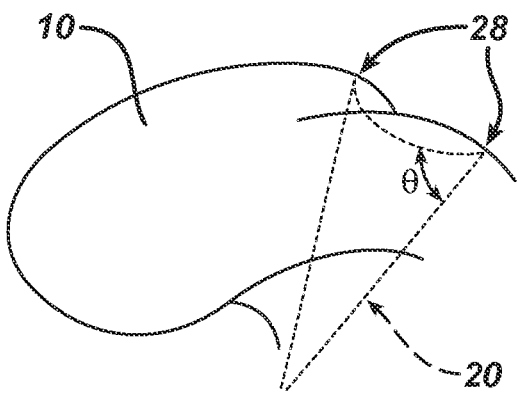
FIG. 6 depicts a benefit of the present invention in its ability to reduce the included angle of securement fibers that have a low angle of inclusion.

This reduction in diameter or cross-sectional area provides discrete areas that may serve as hinges in the material to enable a reduced bend radius of curvature. The reduced diameter sections may also be subjected to the creation of a preformed shape after the fiber drawing has occurred to provide tighter bend radii after installation in tissue. During installation, the preformed arc will open elastically and upon final installation, the fiber will return to the preformed closed configuration. This feature is particularly useful in applications where the fiber is installed through single puncture sites 28 with fiber 20 folded back over itself ends at included angles of the fiber that are less than 180° such as shown in FIG. 6. The utility of the angle is greatest at angles of approximately 90° or less.

The resultant fiber provides both increased elongation and large tissue load bearing surfaces to adapt to excessive loading without cutting through the tissues, while providing a small bend radius, or included bend angle, at the locations of installation to minimize the volume of material located at the puncture site such as those utilized in the installation of tongue suspension fibers as shown in FIG. 6.

B. Fibers of Reduced Diameters Through Volume Compaction

A second method for producing securement fibers of reduced cross sectional area or diameters is by compacting of expanded type fiber forms, such as ePTFE. When materials such as ePTFE are utilized, the localized hinge points are created through the use of volume compaction and re-sintering of the material. ePTFE is formed as an expanded Teflon material with free volume located similar to a closed cell foam structure. The material is formed through a paste extrusion and is then subjected to a sintering process to cause bonding of the nodules of material to create a fiber with adequate strength and a high degree of suppleness. When the fiber is produced with larger cross-sectional areas or geometries, it provides a material with good load bearing surfaces to resist tissue cutting during loading without compromising flexibility. As noted earlier, one issue with unmodified fibers relates to the volume of material at the locations of single puncture placements such as those described previously. In these discrete locations, the relatively incompressible closed cell foam like structure can be too bulky and may prop the puncture open during the healing of the tissue (such as depicted in FIG. 3) This propping of the tissue may provide adequate access for pathogens, particularly in tissues with low vascularity.

Figure 5A:
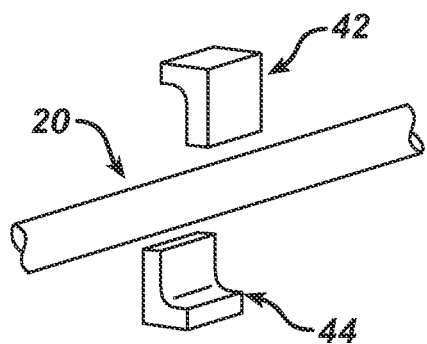
FIGS. 5*a*-5*c* depict a second method of reducing the cross sectional area of a tissue securement fiber as well as a tissue securement fiber of reduced cross sectional area.
Figure 5B:
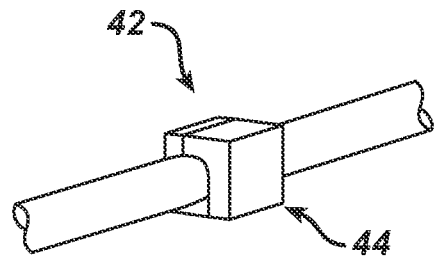
Figure 5C:
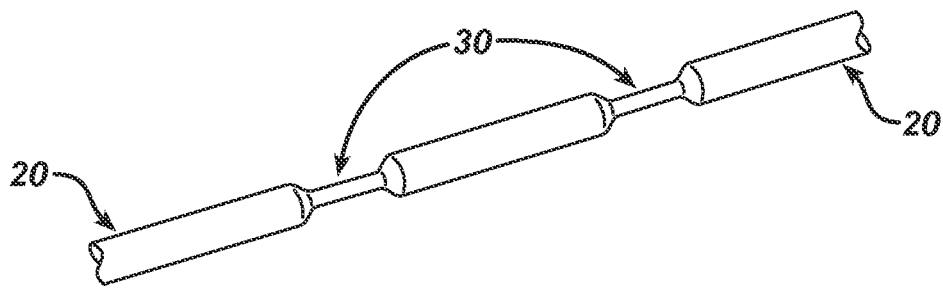

Referring to FIG. 5a, fiber 20 is placed within preferably heated or energized compaction dies 42 and 44 and is subjected to temperatures similar to those utilized in the sintering process (see FIG. 5b). This enables a reduction/removal of the inter-nodal dead space and a reduction in the cross-sectional area of the fiber. Again, these reduced volume areas provide natural hinging points 30 in the fiber 20 (see FIG. 5c) that when bent at the site of single puncture insertions, reduces the tendency of the fiber to prop the puncture open.

The compaction of the ePTFE fiber is achieved through the application of thermal heating to elevate the temperature of the local region of the fiber to approximately 342° C. to 380° C. The material is compressed within the dies during the heating process until at least a portion of the intermodal distance is reduced and fused into a tighter spacing. This reduction in intermodal spacing serves to reduce the volume of the fiber, however, unlike the drawing process previously described, no elongation of the fiber is necessary to create the reduced diameter region in the fiber.

In either method described above, the fibers exhibit a reduced cross-sectional area at discrete locations to facilitate improved bending and reduced volume to prevent tissue propping of the installation puncture sites. Additionally, the reduced cross sectional area regions of the fiber may be formed with preset curved (arc) or bent geometries that will serve to provide tighter bend radii in the fiber at the preferred discrete bending locations.

Figure 7:
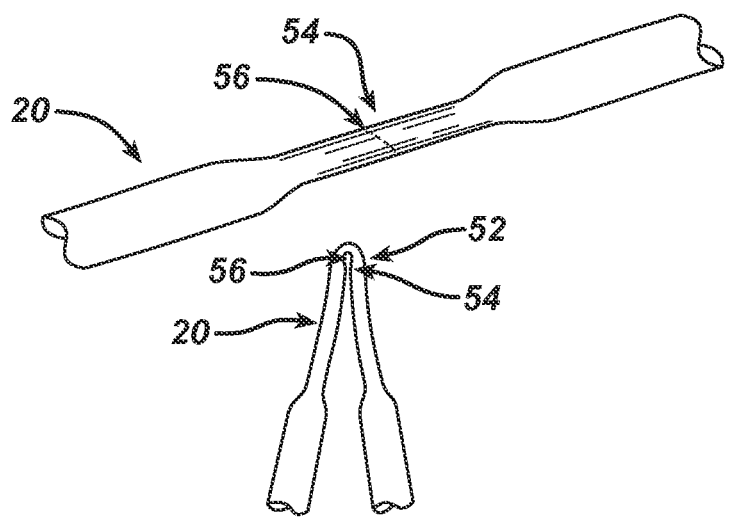
FIG. 7 shows one embodiment for a securement fiber of the present invention that includes a bending crease or indentation.

In addition to or in combination with either method described above, the fiber may be further compacted in a controlled manner at specific, discrete locations. Such compacting may simply involve forming a crease or indentation across the diameter of the fiber to form a more discrete, hinge-like bending zone. Referring to FIG. 7, fiber 20 contains a zone of reduced cross sectional area 54 which further contains crease or indentation 56. Crease or indentation 56 is shown to enable bending of fiber 20 about bending point 52. Crease or indentation 56 thus provides a more discrete point for the bending of fiber 20 in addition to the reduced volume of the fiber 20 along the reduced cross sectional area 54.

Figure 8:
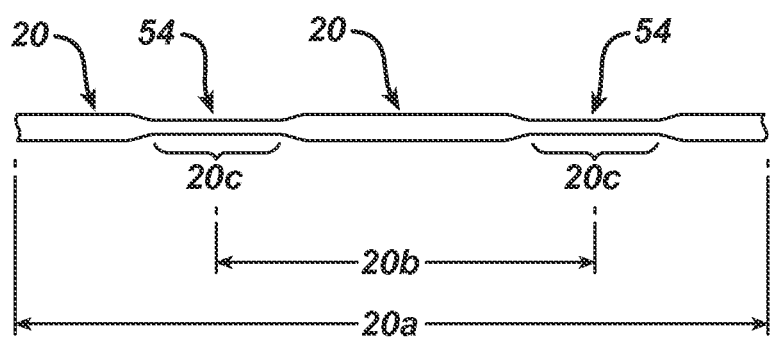
FIG. 8 represents one embodiment of a securement fiber of this invention.

The fibers may be produced with one or more reduced cross sectional regions on the fiber. The number of zones of multiple cross sectional reductions on a single fiber will depend on the intended use. For example, in the instance of performing a tissue securement procedure as described in FIG. 6, at least two zones of reduced cross sectional area are needed. FIG. 8 represents one preferred embodiment of the invention for the instance that the fiber is used for tongue suspension. Referring to FIG. 8, the overall length 20a of fiber 20 may range from approximately 30 to 40 cm, the distance 20b between the center points of the two zones of reduced cross sectional area 24 may range from 1 cm to 3 cm, preferably 2 cm and the lengths 20c of the reduced regions 54 may range from 0.3 cm to 1.0 cm, preferably 0.5-0.7 cm. It should be noted that the respective lengths 20c of the two section 54's depicted, need not be of equal length.

Additionally, the degree of diameter reduction of the securement fiber may play a role for an intended application. It is contemplated that for tissue securement applications for treating obstructive sleep apnea, the reduction in cross sectional area will range from the original cross sectional area to the reduced cross sectional area from 4:1 to 10:1, preferably from 6:1 to 9:1, most preferably from 3:1

It should be understood that the foregoing disclosure and description of the present invention are illustrative and explanatory thereof and various changes in the size, shape and materials as well as in the description of the preferred embodiment may be made without departing from the spirit of the invention.

What is claimed is:
1. A monolithic tissue securement fiber comprising:
   at least two sections having a first cross sectional area and each section having first lengths that may be the same or not;
   at least one section having a second cross sectional area and a second length; and transition sections between the at least two sections having a first cross sectional area and the at least one section having a second cross sectional area,
wherein the second cross sectional area is less than the first cross sectional area and the at least one section having the second cross sectional area is intermediate to the at least two sections having the first cross sectional area and wherein the transition sections from the at least two sections having a first cross sectional area to the at least one section having a second cross sectional area is a transition of continuous reduction in cross sectional area with the reduced cross sectional area having a continuous perimeter and wherein the second length is shorter than any of the first lengths.

2. The fiber of claim 1, wherein the at least one section having the second cross sectional area further comprises an arc.

3. The fiber of claim 1, wherein the at least one section having the second cross sectional area further comprises an indentation.

4. The fiber of claim 1, wherein the ratio of the first cross sectional area to the second cross sectional area ranges from 4:1 to 10:1.

5. The fiber of claim 4, wherein the ratio of the first cross sectional area to the second cross sectional area ranges from 6:1 to 9:1.

6. The fiber of claim 4, wherein the ratio of the first cross sectional area to the second cross sectional area is 9:1.

7. The fiber of claim 1, wherein the fiber is comprised of a combination of a bioabsorbable and non-bioabsorbable materials.

8. The fiber of claim 1, wherein the fiber is comprised of a biocompatible polymer selected from the group consisting of polyamides, polyesters, fluoropolymers, polyaryletherketones, polyolefins, and combinations thereof.

9. The fiber of claim 8 wherein the polyamide is selected from the group consisting of polyhexamethylene adipamide (nylon 66), polyhexamethylene sebacamide (nylon 610), polycapramide (nylon 6), polydodecanamide (nylon 12), polyhexamethylene isophthalamide (nylon 61), and combinations thereof.

10. The fiber of claim 8, wherein the polyester is selected from the group consisting of polyethylene terephthalate, polybutyl terephthalate, and combinations thereof.

11. The fiber of claim 8 wherein the fluoropolymer is selected form the group consisting of polytetrafluoroethylene, polyvinylidene fluoride, poly (hexafluoropropylene-VDF) and combinations thereof.

12. The fiber of claim 8, wherein the polyolefin is selected from the group consisting of polypropylene, isotactic polypropylene, syndiotactic polypropylene, and combinations thereof, and combinations of predominately isotactic or syndiotactic polypropylene with heterotactic polypropylene and/or polyethylene.

13. The fiber of claim 1, wherein the fiber is comprised of a bioabsorbable polymer selected from the group consisting of aliphatic polyesters, alkyl derivatives of trimethylene carbonate, δ-valerolactone, β-butyrolactone, γ-butyrolactone, ε-decalactone, hydroxybutyrate, hydroxyvalerate, 1,4-dioxepan-2-one (including its dimer 1,5,8,12-tetraoxacyclotetradecane-7,14-dione), 1,5-dioxepan-2-one, 6,6-dimethyl-1,4-dioxan-2-one and polymer blends thereof.

14. The fiber of claim 13, wherein the aliphatic polymer is selected from the group consisting homopolymers and copolymers of lactic acid, d- l- and meso lactide, glycolide, glycolic acid, ε-caprolactone, p-dioxanone (1,4-dioxan-2-one), trimethylene carbonate (1,3-dioxan-2-one), and combinations thereof.

15. The fiber of claim 1, wherein the fiber is poly (hexafluoropropylene-VDF) or polypropylene.

* * * * *